United States Patent [19]

Nacamuli et al.

[11] Patent Number: 4,584,423

[45] Date of Patent: Apr. 22, 1986

[54] XYLENE ISOMERIZATION USING A ZEOLITE WITH A GROUP II METAL

[75] Inventors: Gerald J. Nacamuli, Mill Valley; Donald A. Hickson, Benicia, both of Calif.

[73] Assignee: Chevron Research Company, San Francisco, Calif.

[21] Appl. No.: 753,294

[22] Filed: Jul. 9, 1985

Related U.S. Application Data

[63] Continuation of Ser. No. 635,676, Jul. 30, 1984, abandoned, which is a continuation-in-part of Ser. No. 533,712, Sep. 19, 1983, abandoned.

[51] Int. Cl.[4] .................................................. C07C 5/22
[52] U.S. Cl. .................................. 585/481; 502/71; 502/77
[58] Field of Search .................. 585/481, 480; 502/71, 502/77

[56] References Cited

U.S. PATENT DOCUMENTS

| | | | |
|---|---|---|---|
| Re. 30,157 | 11/1979 | Burress | 585/481 |
| 4,159,283 | 6/1979 | Nicoletti et al. | 585/481 |
| 4,224,141 | 9/1980 | Morrison et al. | 585/481 |
| 4,227,728 | 1/1981 | Rubin et al. | 585/481 |
| 4,351,979 | 9/1982 | Chester et al. | 585/481 |

Primary Examiner—John Doll
Assistant Examiner—A. Pal
Attorney, Agent, or Firm—J. A. Buchanan, Jr.; T. G. DeJonghe

[57] ABSTRACT

A process for isomerizing xylenes containing ethylbenzene to obtain near equilibrium amounts of paraxylene and to convert the ethylbenzene to hydrocarbons readily removable from the xylenes. The isomerization reaction uses a ZSM-5 type catalyst with 0.05 to 1.5 percent of an added metal such as zinc, cadmium, or barium. The isomerization is carried out in the absence of added hydrogen at low pressure, preferably between about 0 and 200 psig. Relatively low xylene losses are achieved even at high ethylbenzene conversion levels.

9 Claims, 3 Drawing Figures

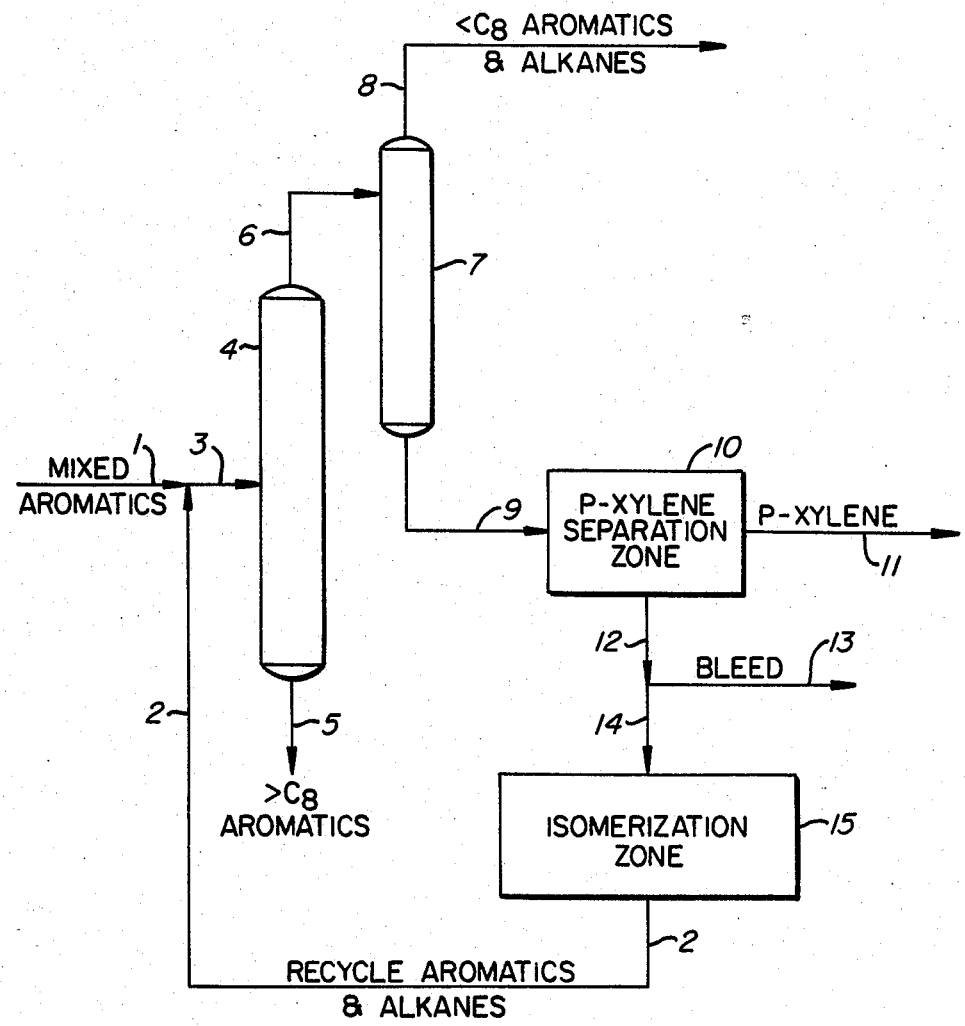
FIG._1.

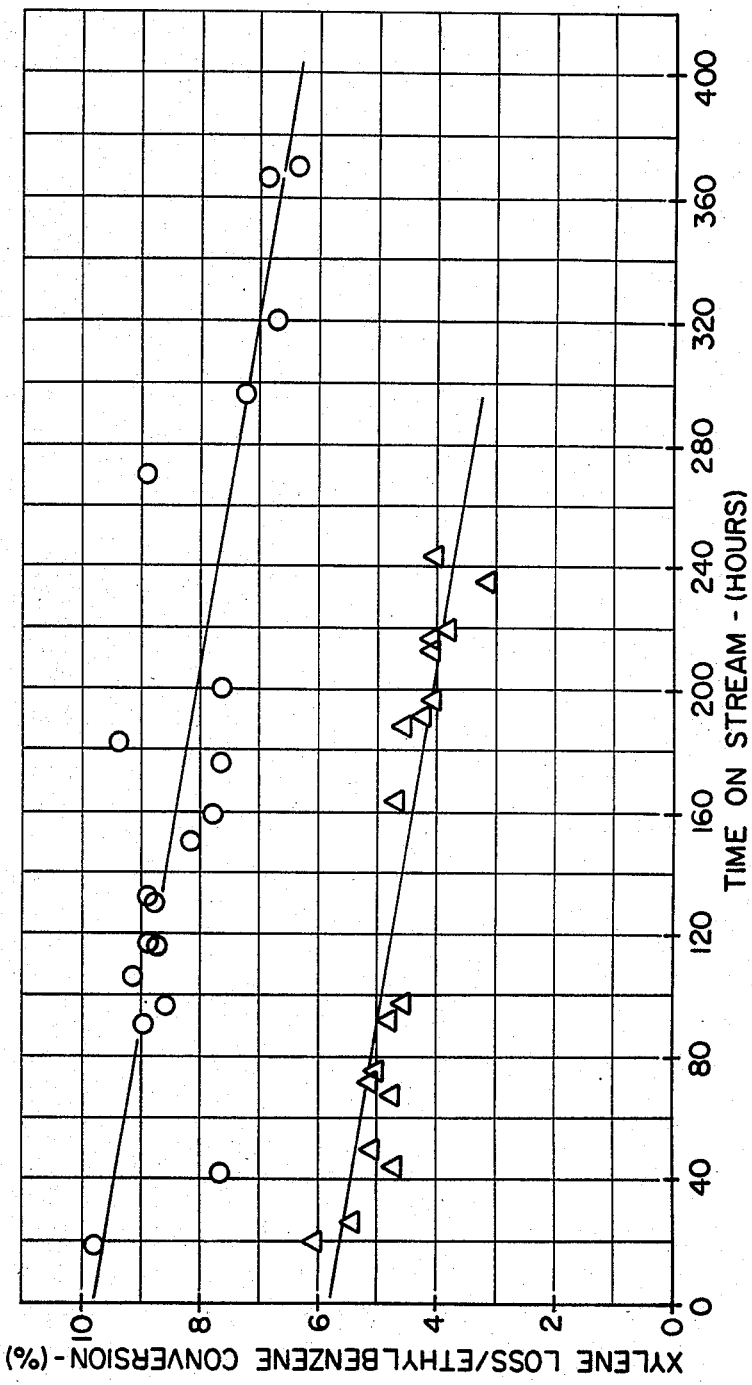

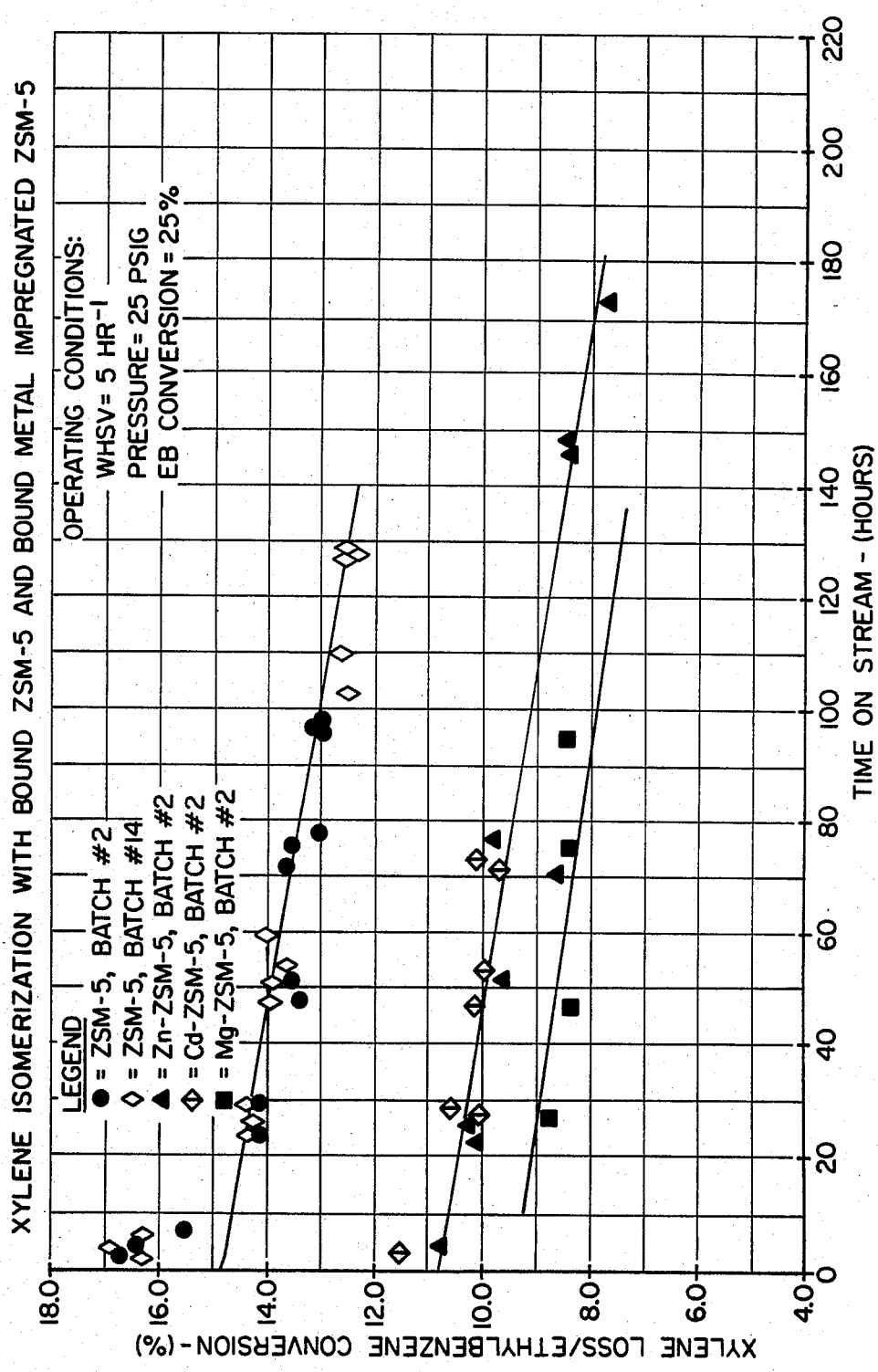

XYLENE ISOMERIZATION USING A ZEOLITE WITH A GROUP II METAL

RELATED APPLICATION

This is a continuation of application Ser. No. 635,676, filed Jul. 30, 1984 now abandoned, which is a continuation-in-part of Ser. No. 533,712, filed Sept. 19, 1983.

FIELD OF THE INVENTION

The present invention relates to the isomerization of xylenes using a crystalline alumino-silicate catalyst.

BACKGROUND OF THE INVENTION

The xylenes, namely orthoxylene, metaxylene and paraxylene, are important chemicals and find wide and varied application in industry. Orthoxylene is a reactant for the production of phthalic anhydride. Metaxylene is used in the manufacture of plasticizers, azo dyes, wood preservers, etc. Paraxylene upon oxidation yields terephthalic acid which is used in the manufacture of synthetic textile fibers.

As a result of the important applications to which the individual xylene isomers are subjected, it is often very important to be able to produce high concentrations of a particular xylene. This can be accomplished by converting a nonequilibrium mixture of the xylene isomers, which mixture is low in the desired xylene isomer, to a mixture which approaches equilibrium concentrations. Various catalysts and processes have been devised to accomplish the isomerization process. For example, it is well known in the art that catalysts such as aluminum chloride, boron fluoride, liquid hydrofluoric acid, and mixtures of hydrofluoric acid and boron fluoride can be used to isomerize xylene mixtures.

Another well-known xylene isomerization catalyst is amorphous silica alumina, having the trade name "Durabead".

A typical processing scheme for producing paraxylene comprises:

(a) isomerizing a $C_8$ alkylaromatic mixture to near equilibrium in an isomerization reaction zone;

(b) separating out paraxylene as by low temperature crystallization, to obtain a paraxylene-rich stream and a stream rich in other xylenes; and (c) recycling the stream rich in other xylenes to the isomerization reaction zone.

The present invention is particularly concerned with the isomerization reaction step which may be used in an overall process directed to paraxylene production.

Numerous catalysts have been proposed for use in xylene isomerization processes such as mentioned above. More recently, a number of patents have disclosed the use of catalysts containing molecular sieves or zeolites for isomerization of $C_8$ alkylaromatics. For example, U.S. Pat. No. 3,790,471 discloses the use of a zeolite identified as ZSM-5 for hydroconversions such as isomerization of polyalkyl substituted aromatics, for example, orthoxylene.

ZSM-5 is a crystalline aluminosilicate zeolite having intermediate size pores. Various zeolites having intermediate size pores are described in commonly assigned U.S. patent application Ser. No. 305,679 of S. J. Miller. Ser. No. 305,679 is not directed to isomerization but rather is directed to oligomerization of olefins using a catalyst comprising ZSM-5 impregnated with zinc or cadmium.

Isomerization reactions using crystalline aluminosilicate zeolite catalysts may be carried out in the presence of added hydrogen. See for example, U.S. Pat. No. 4,331,822, Onodera et al., which discloses vapor phase isomerization in the presence of added hydrogen using a crystalline aluminosilicate zeolite such as ZSM-5 and wherein the zeolite contains at least two metals which are (a) platinum and (b) at least one metal selected from the group consisting of titanium, chromium, zinc, gallium, germanium, strontium, yttrium, zirconium, molybdenum, palladium, tin, barium, cesium, cerium, tungsten, osmium, lead, cadmium, mercury, indium, lanthanum, beryllium, lithium and rubidium.

The process described in U.S. Pat. No. 4,331,822 is carried out at pressures in the range of 100 to 200 psig in the presence of hydrogen. U.S. Pat. No. 3,281,482 discloses isomerization using a crystalline aluminosilicate of the zeolite type at pressures preferably of 500 to 1000 psig.

U.S. Pat. No. 3,856,873 discloses an isomerization reaction operating at pressures of about 0 to 1000 psig, and temperatures of about 500° F. to 1000° F., maintaining vapor phase reaction conditions. The catalyst used in the '873 process is a ZSM-5 zeolite. The zeolite can be used alone or with an added metal such as nickel. Typically, the zeolite used in the '873 process also is combined with alumina, the alumina serving as a binder material in which the zeolite is embedded to form an attrition-resistant catalyst pellet.

U.S. Pat. No. 3,856,873 points out at column 6, line 40, that, "Since the process is conducted in the absence of added hydrogen, there is no need for metals of the transition group such as nickel, platinum, palladium, etc. These metals may be present, but as now understood, the process appears to be unaffected by such cations."

Other patents directed to xylene isomerization using zeolitic catalysts with added hydrogen include U.S. Pat. No. 4,163,028, which discloses use of ZSM-5 having a silica to alumina ratio of at least 500 and wherein the isomerization temperature is greater than 800° F.; U.S. Pat. No. 3,856,872, which discloses isomerization using ZSM-5, ZSM-11, or ZSM-12; U.S. Pat. No. 4,218,573, which discloses use of ZSM-5 containing alkali metal cations such as sodium; and U.S. Pat. No. 4,101,596, which discloses isomerization without added hydrogen, using a ZSM-5 catalyst at a pressure less than 100 psig, a temperature between 500° F. and 800° F., and using an alkylaromatic feed which is essentially free of peroxide. U.S. Pat. No. 4,159,282 to Olson discloses a xylene isomerization process that preferably is carried out in the presence of hydrogen. Olson uses a catalyst having a crystalline aluminosilicate zeolite with a crystal size of at least 1 micron, and ZSM-5 is a preferred aluminosilicate for use in his process. To control xylene sorption characteristics of his catalyst, preferably P, B, Mg, or Sb oxides are included in the catalyst. Example 7 uses 6.0 weight percent Mg O, which is about 3.6 weight percent expressed as Mg.

SUMMARY OF THE INVENTION

According to the present invention, a process is provided for isomerization of a nonequilibrium mixture of xylenes containing ethylbenzene which comprises:

(a) feeding the mixture of xylenes to a xylene isomerization reaction zone;

(b) contacting the mixture in the reaction zone with a ZSM-5 type zeolite catalyst containing zinc, cadmium, iron, barium, tin or cesium metal, thereby isomerizing the xylenes; and (c) carrying out the xylene isomerization in the absence of added hydrogen, and at vapor phase reaction conditions. Preferred vapor phase reaction conditions include a pressure between atmospheric and 200 psig and a temperature between 500° F. and 800° F.

Preferred metals for use in the catalyst include zinc, cadmium, iron and barium. We have found zinc and cadmium particularly preferred for the present isomerization process. We have found that advantageous results are achieved in terms of reduced xylene loss if the amount of metal is between 0.05 and 1.5 weight percent, more preferably 0.1 to 1.0 weight percent based on the weight of zeolite in the catalyst.

Among other factors, the present invention is based on our finding that using a zeolite catalyst such as ZSM-5 with an added metal such as zinc or cadmium, and at a metals level between 0.05 and 1.5 weight percent, in a low pressure, vapor phase isomerization reaction without added hydrogen, results in unexpectedly low xylene losses at high ethylbenzene conversion.

In isomerization of xylenes, it is desirable to convert ethylbenzene to other components, such as benzene, ethylbenzene and $C_9+$ alkylaromatics, as such other components may be separated from xylenes readily by distillation. Ethylbenzene itself is costly to separate from xylenes by fractional distillation. By converting the ethylbenzene to other components, build-up of ethylbenzene in the recycle to the isomerization reaction zone can be reduced. However, as severity of isomerization conditions are increased to increase the ethylbenzene conversion, loss of xylenes due to disproportionation, transalkylation and cracking reactions, etc., increases.

In the present invention, xylene losses as low as 1.0 to 1.4 percent at ethylbenzene conversions of about 22 to 28 percent have been achieved, whereas using a ZSM-5 catalyst without the added metal such as zinc or cadmium resulted in xylene losses of 1.5 to 2.6 percent at ethylbenzene conversions of about 22 to 28 percent.

Reaction conditions which are preferred for the isomerization reaction in accordance with the present invention include a temperature of between about 500° F. and 750° F., more preferably between about 550° F. and 700° F. These temperatures are start-of-run temperatures. End-of-run temperatures should be 150° F. to 200° F. higher than start-of-run temperatures.

The isomerization reaction of the present invention is carried out in the absence of added hydrogen. The pressure in the isomerization zone is preferably between atmospheric and 200 psig, more preferably between 10 and 100 psig. The pressure and temperature are such as to maintain vapor phase reaction conditions for the isomerization. Particularly preferred pressure is about 20 to 30 psig for the isomerization reaction.

Preferred feeds for the process of the present invention are $C_8$ alkylaromatic feedstocks which can be isomerized to convert xylenes, such as orthoxylene and metaxylene, to paraxylene. Typical $C_8$ aromatic feeds are obtained from catalytic reforming of naphthas. Typically, the product from the catalytic reformer is fed to an aromatics extraction plant, e.g., Sulfolane, where the aromatics ($C_8$ or BTX) are separated from the paraffins or non-aromatics. After recovering the $C_8$ aromatics portion from the aromatics stream, the $C_8$ aromatics stream is then fed to a xylene "loop" as shown in FIG. 1 described below.

Preferred weight hourly space velocities for the feed over the zeolite isomerization catalyst are between 1 and 10, more preferably between 3 and 7, based on the zeolite portion of the catalyst.

The ZSM-5 zeolite component of the catalyst used in the process of the present invention can be prepared in various manners. Suitable preparation procedures are described in U.S. Pat. No. 3,702,886 to Argauer et al. Also, an exemplary procedure is set forth in the Examples which follow below.

ZSM-5 embraces a family of crystalline aluminosilicates as set forth in more detail in U.S. Pat. No. 3,702,886, the disclosure of which patent is incorporated by reference into this specification.

The structure of the ZSM-5 class of zeolites is such that the pore sizes or apertures of the zeolite are in the intermediate size range of approximately 5 to 7 Angstroms, usually about 5.5 Angstroms. This is in contrast to the larger pore size zeolites such as faujasite or the smaller pore size zeolites such as Linde Type A and erionite. The structure of ZSM-5 is described by Kokotailo et al. in *Nature*, Vol. 272, Mar. 30, 1978, page 437. The pore opening into the crystalline zeolite is delineated by the atomic structure.

Although ZSM-5 is the preferred zeolite for use in the catalyst used in the process of the present invention, other zeolites of the ZSM-5 type are embraced within a broad embodiment of the present invention. These zeolites include ZSM-11 which is described in U.S. Pat. Nos. 3,709,979 and 4,108,881 (alternate synthesis), the disclosures of which are incorporated by reference into the present specification.

The ZSM-5 zeolite can be made by preparing a solution containing water, tetrapropyl ammonium hydroxide and the elements of sodium oxide, an oxide of aluminum or gallium, an oxide of silica, and having a composition, in terms of mole ratios of oxides, falling within the following ranges:

TABLE 1

|  | Broad | Preferred | Particularly Preferred |
|---|---|---|---|
| $OH^-/SiO_2$ | 0.07–1.0 | 0.1–0.8 | 0.2–0.75 |
| $R_4N^+/(R_4N^+ + Na^+)$ | 0.2–0.95 | 0.3–0.9 | 0.4–0.9 |
| $H_2O/OH^-$ | 10–300 | 10–300 | 10–300 |
| $SiO_2/Al_2O_3$ | 5–100 | 10–60 | 10–40 | wherein R is propyl. This mixture is maintained at reaction conditions until the crystals of the zeolite are formed. Thereafter the crystals are separated from the liquid and recovered. Typical reaction conditions consist of a temperature of from about 160° F. to 400° F. for a period of about 2 days to 60 days. A more preferred temperature range is from about 190° F. to 235° F., with the amount of time at a temperature in such range being from about 7 days to 21 days.

The digestion of the gel particles is carried out until crystals form. The solid product is separated from the reaction medium, as by cooling the whole to room temperature, filtering and water washing.

ZSM-5 is preferably formed as an aluminosilicate. The composition can be prepared utilizing materials which supply the elements of the appropriate oxide. Such compositions include aluminosilicate, sodium aliminate, alumina, sodium silicate, silica hydrosil, silica gel, silicic acid, sodium hydroxide and tetrapropylammonium hydroxide. Each oxide component utilized in the reaction mixture for preparing a member of the ZSM-5 family can be supplied by one or more initial reactants. For example, sodium oxide can be supplied by an aqueous solution of sodium hydroxide, or by an aqueous solution of sodium silicate. The reaction mixture can be prepared either batchwise or continuously. Crystal size and crystallization time of the ZSM-5 composition will vary with the nature of the reaction mixture employed. The zeolite contains tetrapropylammonium cations which are removed by calcination producing the H-Na form of the zeolite.

The zeolites used in the instant invention usually have a certain proportion of the original cations associated therewith replaced by a wide variety of other cations according to techniques well known in the art. Typical replacing cations include hydrogen, ammonium and metal cations including mixtures of the same. Preferably, the replacing cation is hydrogen.

Typical ion exchange techniques include contacting the zeolite with a salt of the desired replacing cation or cations. Although a wide variety of salts can be employed, particular preference is given to chlorides, nitrates and sulfates.

In the process of the present invention, it is preferred to use the zeolite in a "bound" form, that is, with a refractory oxide as a binder for the overall catalyst particle. Suitable refractory oxide binders are alumina, silica, titania, clay, or mixtures thereof. This binder serves to hold the crystalline zeolite particles together in a catalyst particle of suitable size and suitable attrition resistance upon handling and use in the isomerization process. The amount of binder used versus zeolite is preferably between 10 and 65 percent binder by weight, more preferably between 20 and 50 percent binder.

Alumina is a particularly effective binder for the catalyst used in the isomerization process of the present invention. A preferred form of the alumina is that commonly referred to as Catapal-SB, available from Conoco Chemical Division of Continental Oil Company.

A typical catalyst is in the form of a 1/16 inch diameter by 3/16 inch length extrudate. Use of the zeolite catalyst as prepared would result in too high a pressure drop in the preferred fixed catalyst bed used in the isomerization process.

The added metal, such as the preferred zinc, cadmium or barium used in the isomerization catalyst, may be added to the catalyst by impregnation using known techniques. In general, the metals are added as salts, preferably of thermally decomposable anions such as the nitrate, nitrite, acetate, etc., or soluble metal complexes, by filling the pores of the catalyst with a solution of appropriate concentration to achieve the desired metal loading, equilibrating, drying and calcining to remove solvent, impurities and to decompose the salts to remove the volatile products. Alternatively, ion exchange, adsorption or other techniques well known to the are for introducing metals into porous substances may also be used.

BRIEF DESCRIPTION OF THE DRAWINGS

FIG. 1 of the drawings is a schematic flow diagram illustrating the positioning of the isomerization reaction zone in a process sequence directed to producing paraxylene.

FIG. 2 is a graph comparing xylene isomerization using ZSM-5 with no added zinc versus use of ZSM-5 with added zinc.

FIG. 3 is a comparison along the lines of FIG. 2, except that here the zeolite is combined with a binder.

DETAILED DESCRIPTION AND EXAMPLES

Referring now in more detail to FIG. 1, a mixed aromatic feed in line 1, previously treated to remove nonaromatic components, is combined with the line 2 effluent stream from isomerization zone 15. The combined streams are fed via line 3 to column 4 for distillation. The higher boiling aromatics—those having more than 8 carbon atoms—are taken as a bottoms fraction in line 5; the overhead comprising $C_8$ aromatics and lighter components is charged via line 6 to another distillation unit column 7. In this second distillation column, the lower boiling aromatics—those having less than 8 carbon atoms—and any paraffinic components are taken overhead in line 8. The bottoms from the second distillation column, comprising essentially all $C_8$ aromatics, are then fed via line 9 to paraxylene separation zone 10, wherein about 25 to 95 percent of the paraxylene is removed by crystallization or by extraction, e.g., the UOP "Parex Process", and paraxylene is withdrawn via line 11. The effluent (mother liquor) from the paraxylene plant is then withdrawn via line 12 and is fed to the isomerization zone 15. Provision is made via line 13 to bleed some of paraxylene plant mother liquor as desired. Finally, the xylene isomerized stream from the isomerization zone 15 is recycled to be combined with the incoming fresh feed. Typical fresh feed to such a combined process contains about 5 to 30 percent ethylbenzene based on $C_8$ aromatics. The recycle stream contains about 5 to 20 percent ethylbenzene based on $C_8$ aromatics. When operating this process in a continuous manner, the quantity of recycled $C_8$ aromatics is from 2 to 4 times that of the fresh feed; and the ethylbenzene in the feed to the paraxylene plant levels out at about 5 to 25 percent.

EXAMPLE 1

Preparation of the ZSM-Type Zeolite 1.44 lbs. of sodium aluminate, Matheson, Coleman and Bell suppliers, (% by weight $Na_2O=33$, % by weight $Al_2O_3=48$) were dissolved in 72.05 lbs. of distilled water in a polypropylene vessel. 14.85 lbs. of tetrapropylammonium bromide (97%) was dissolved in 144 lbs. of water and added with vigorous stirring to the sodium aluminate solution in the tank. 115 lbs. of "N" sodium silicate (% by weight, $Na_2O=8.87$, $SiO_2=28.33$, $H_2O=62.8$) were dissolved in 288 lbs. of distilled water. In another vessel, 11.5 lbs. of concentrated sulfuric acid were dissolved in 720 lbs. of water. The acid solution and silicate solution were added simultaneously to the stirred aluminate solution and vigorously mixed until gellation occurred. The tank was heated to 190°-200° F. for 24 hours at which time the stirring was restarted and continued while heating to 280° F. for 16 days. A crystalline product was recovered by freeze-filtration, washed with ammonium acetate solution and water, dried at 220° F., and finally calcined in air for 10 hours at 1000° F. The product was identified by X-ray diffraction analysis as greater than 90% ZSM-5 type zeolite. Analysis showed the product to be ~1 micron aggregates made up of 0.04–0.05 micron crystallites.

Purification of the Zeolite Product

The calcined zeolite product was mixed with 5 wt. % Keltrol (a xanthan gum product, Keltrol Co., Clark, N.J.) and water to form an extrudable paste. The plastic mass was extruded through a 1/16" die to form cylindrical extrudate. The product was dried 16 hours at 120° C. in 20" $N_2$-vacuum to give a strong extrudate pellet. This product was ion exchanged with 10 vol. per weight of catalyst using 2 normal ammonium acetate in 50/50 isopropanol/water at 80° C. four times. After rinsing twice with isopropanol, the product was washed with cold water twice and dried 16 hours at 120° C.

EXAMPLE 2

Preparation of the Hydrogen-ZXM Zeolite Catalyst

A portion of the ammonium-exchanged extrudate prepared as described above was calcined in air for 10 hours at 539° C. The product was identified by X-ray analysis to be ZSM-5 of greater than 90% crystallinity. Sodium was less than 0.11% by weight by analysis.

EXAMPLE 3

Preparation of the Zinc-Hydrogen-ZSM Zeolite Catalyst

A portion of the ammonium-exchanged extrudate prepared as described in Example 2 was impregnated with zinc acetate solution to provide a product containing 0.5 wt. % zinc. The product was dried 16 hours at 100° C. in 20" Hg $N_2$-vacuum and finally calcined in air 10 hours at 538° C. The product contained 0.50% zinc by analysis.

EXAMPLE 4

Preparation of the 1/16" ZSM (65 wt. %)Alumina (35 wt. %) Catalyst

To 34.8 gms of the hydrogen zeolite prepared as in Example 2 was added 25.2 gms of Catapal-SB (Loss on Ignition=27.17%) (Conoco Chemical Division of Continental Oil Company, U.S.A.). The solids were thoroughly inter-dispersed. A solution of 1.17 gms of nitric acid (70%) in 35.0 gms water was sprayed onto the mixing powders and mulled to a uniform plastic mass which was heated 50 minutes at 100° C. The cooled mass was extruded through a 1/16" die twice, dried 5 hours at 100° C. in 20" Hg $N_2$-vacuum, and calcined 10 hours at 538° C. in air.

EXAMPLE 5

Preparation of 1/16" 0.5 wt. % Zn-H-ZSM (65 wt. %)Alumina (35 wt. %) Catalyst 0.52 gm of zinc acetate was dissolved in 52 gms of distilled water. This solution was sprayed over 32 gms of the hydrogen zeolite powder prepared as in Example 2 and mixed until homogeneous. The powder was dried 5 hours at 100° C. in 20" $N_2$-vacuum. The whole product was mixed with 22.5 gms of Catapal-SB alumina hydrate and thoroughly mixed. A solution of 1.17 gms nitric acid (70% $HNO_3$) in 35.1 gms of water was sprayed onto the powder mix and mulled to a homogeneous consistency. After heating 50 minutes at 100° C., the mass was extruded through a 1/16" die twice. After drying 5 hours at 100° C. in 20" Hg $N_2$-vacuum, the product was calcined 10 hours in air at 538° C. The product contained 0.46% zinc by analysis (based on zeolite content).

Note: Cadmium, barium, and magnesium catalysts were prepared as described in Example 5 maintaining constant or equivalent atom concentrations of each metal to zinc in Example 5.

EXAMPLE 6

A $C_8$ aromatic feed with a non-equilibrium concentration of xylenes was passed over unbound (no alumina support) ZSM-5 to isomerize the xylenes to equilibrium. The feed was the mother liquor from a commercial unit producing paraxylene (PX) by crystallization and hence has a concentration of PX which is below equilibrium. The feed composition is shown in Table 2. This feed was passed over 2.09 gms of unbound ZSM-5 at a rate of 10.40 gm/hr (12 cc/hr) to yield a weight hourly space velocity (WHSV) based on the catalyst of 4.98 hour$^{-1}$.

The reactor consisted of a 0.5" diameter 316 SS tube. Reactor length was 26". The reactor was first filled to about half its height with inert 38 Alundum, size 20 grit (Norton Company, Worcester, Mass. 01606). The reactor with the Alundum was vibrated to tightly pack the inert material. The catalyst, ZSM-5, was then added, followed by more Alundum until the reactor tube was completely packed. The section of Alundum above the active catalyst acts as a preheater and ensures that the feed is totally vaporized by the time it contacts the catalyst.

The ZSM-5 catalyst was in extrudate form with a diameter of 1/16" and a length of 2/16" to 3/16".

The start-of-run temperature was 600° F. and the reactor pressure was controlled at 25 psig throughout the run. During the run, the reactor temperature was continuously adjusted upwards to maintain an ethylbenzene conversion of about 25 wt. %. The temperature adjustments are necessary to compensate for loss of activity due to the aging of the catalyst.

The ethylbenzene conversion was determined by gas chromatographic analysis of the total reactor effluent by means of an in-line sampling valve. Liquid product was collected over 1-hour periods and also analyzed by gas chromatography. The volume of off-gas produced was also measured and analyzed. However, the quantity of off-gas was so small that representative samples could not be obtained. The analysis of the off-gas shows 98.35% inerts, nitrogen plus oxygen, and 1.65% hydrocarbons. This yields an off-gas rate of <0.1 wt. % of the feed to the reactor.

Reaction conditions and analysis of the liquid product collected over 1-hour periods at 18–19, 89–90 and 159–160 hours on-stream is shown in Table 2.

A similar experiment was carried out using an unbound ZSM-5 catalyst impregnated with zinc. The zinc content was 0.5 wt. % of the ZSM-5. Reaction conditions and liquid product analysis are also listed in Table 2.

Comparison of the results of these two experiments shows that at the same time on-stream, the Zn-ZSM-5 catalyst has a lower xylene loss to ethylbenzene (EB) conversion ratio than the non-metal impregnated ZSM-5. This ratio is useful to use as it allows comparison of the xylene loss between experiments but is referenced by a common (or equal) EB conversion. Thus, at 89–90 hours on-stream, the ZSM-5 catalyst yields a xylene loss to EB conversion ratio of 9.02%. Or, the xylene loss would be 2.26% based on feed at a 25% EB conversion. Similarly, at 92–93 hours on-stream, the Zn-ZSM-5 catalyst yields a xylene loss to EB conversion ratio of 4.84%. This is equivalent to a xylene loss of 1.21% based on feed at a 25% EB conversion. The xylene loss with the Zn-ZSM-5 is 46.3% lower than that obtained with the ZSM-5 catalyst.

For the next example, an improved gas chromatographic method was used to analyze the liquid product. The new method gave different absolute values of xylene loss to ethylbenzene conversion ratio, but the relative amount of improvement remained essentially the same.

EXAMPLE 7

Xylene isomerization experiments were carried out with the catalysts prepared in Examples 4 and 5. The experimental procedure was the same as that described in Example 6.

The Zn-ZSM-5 catalyst contained 0.3 wt. % zinc based on the bound catalyst.

The start-of-run temperature to achieve 25% EB conversion was about 600° F. with ZSM-5 and 645° F. with the Zn-ZSM-5.

The results of these two experiments are compared in Table 3 at about the same time on-stream. As can be seen, at 52 hours on-stream, the ZSM-5 catalyst has a xylene loss to EB conversion ratio of 13.55% while at about the same time on-stream, the Zn-ZSM-5 catalyst has a xylene loss to EB conversion ratio of 9.62%. This is 29% lower than with the ZSM-5 catalyst. Thus, at the same EB conversion, the Zn-ZSM-5 catalyst would have a xylene loss which is 29% lower than that with the ZSM-5 catalyst.

TABLE 2

Xylene Isomerization With Un-Bound ZSM-5 and Zn—ZSM-5

| Catalyst | | ZSM-5 | | | Zn—ZSM-5 (0.5% Zn) | | |
|---|---|---|---|---|---|---|---|
| Hours On-Stream | | 18–19 | 89–90 | 116–117 | 19–20 | 92–93 | 164–165 |
| Reaction Conditions | | | | | | | |
| Temperature, °F. | | 600 | 607 | 615 | 600 | 628 | 646 |
| WHSV, hr$^{-1}$ | | 5 | 5 | 5 | 5 | 5 | 5 |
| Pressure, psig | | 25 | 25 | 25 | 25 | 25 | 25 |
| Component Analysis, Wt. % | Reactor Feed | Liquid Product | | | Liquid Product | | |
| Non-Aromatics | 0.22 | 0.36 | 0.09 | 0.14 | 0.13 | 0.12 | 0.14 |
| Benzene | — | 0.96 | 1.00 | 0.96 | 1.07 | 1.11 | 1.19 |
| Toluene | 0.47 | 1.97 | 1.82 | 1.56 | 1.16 | 1.08 | 1.10 |
| Ethylbenzene | 9.53 | 7.10 | 7.30 | 7.28 | 7.35 | 7.15 | 7.08 |
| Paraxylene | 10.31 | 20.28 | 20.79 | 20.53 | 21.16 | 21.08 | 21.02 |
| Metaxylene | 55.65 | 45.60 | 45.60 | 45.76 | 46.22 | 46.13 | 45.87 |
| Orthoxylene | 22.70 | 20.56 | 20.40 | 20.53 | 20.05 | 20.38 | 20.70 |
| C$_9$+ Aromatics | 1.12 | 3.17 | 3.00 | 3.24 | 2.86 | 2.95 | 2.90 |
| Total | 100.00 | 100.00 | 100.00 | 100.00 | 100.00 | 100.00 | 100.00 |
| Total Xylenes, Wt. % | 88.66 | 86.44 | 86.79 | 86.82 | 87.43 | 87.59 | 87.59 |
| Xylene Loss, % | | 2.50 | 2.11 | 2.08 | 1.39 | 1.21 | 1.21 |
| EB Conversion, % | | 25.50 | 23.34 | 23.61 | 22.88 | 24.97 | 25.71 |
| Xylene Loss/EB Conversion, % | | 9.80 | 9.02 | 8.81 | 6.08 | 4.84 | 4.71 |
| PX Approach to Equilibrium, % | | 96.99 | 101.17 | 98.73 | 103.06 | 104.88 | 102.15 |

(1) Xylene Loss = $\frac{\text{\% Total Xylenes in feed} - \text{\% Total Xylenes in Liquid Product}}{\text{\% Total Xylenes in Feed}} \times 100 = A$ (2) EB Conversion, % = $\frac{\text{Wt. \% EB in Feed} - \text{Wt. \% EB in Liquid Product}}{\text{Wt. \% EB in Feed}} \times 100 = B$ (3) $\frac{\text{Xylene Loss}}{\text{EB Conversion}}$, % = $\frac{A}{B} \times 100$

TABLE 3

Xylene Isomerization With Bound ZSM-5 and Zn—ZSM-5

| Catalyst | | ZSM-5 | | | Zn—ZSM-5 (0.3 Wt. % Zn)* | | |
|---|---|---|---|---|---|---|---|
| Hours On-Stream | | 24 | 52 | 78 | 23 | 53 | 77 |
| Reaction Conditions | | | | | | | |
| Temperature, °F. | | 608 | 615 | 622 | 647 | 649 | 650 |
| WHSV, hr$^{-1}$ | | 5.0 | 5.0 | 5.0 | 5.0 | 5.0 | 5.0 |
| Pressure, psig | | 25 | 25 | 25 | 25 | 25 | 25 |
| Component Analysis, Wt. % | Reactor Feed | Liquid Product | | | Liquid Product | | |
| Non-Aromatics | 0.22 | 0.05 | 0.03 | 0.05 | 0.07 | 0.12 | 0.12 |
| Benzene | — | 0.66 | 0.72 | 0.81 | 1.12 | 1.05 | 1.19 |
| Toluene | 0.47 | 1.94 | 1.91 | 1.94 | 1.50 | 1.38 | 1.47 |
| Ethylbenzene | 9.53 | 7.46 | 7.39 | 7.19 | 7.03 | 7.16 | 6.99 |
| Paraxylene | 10.31 | 20.40 | 20.44 | 20.42 | 20.54 | 20.68 | 20.65 |
| Metaxylene | 55.65 | 46.42 | 46.28 | 46.18 | 46.16 | 46.49 | 46.13 |
| Orthoxylene | 22.70 | 19.10 | 19.25 | 19.23 | 19.61 | 19.36 | 19.57 |
| C$_9$+ Aromatics | 1.12 | 3.96 | 3.98 | 4.18 | 3.97 | 3.76 | 3.88 |
| Total | 100.00 | 100.00 | 100.00 | 100.00 | 100.00 | 100.00 | 100.00 |
| Total Xylenes, Wt. % | 88.66 | 85.93 | 85.87 | 85.82 | 86.31 | 86.53 | 86.35 |
| Xylene Loss, % | | 3.08 | 3.04 | 3.20 | 2.65 | 2.39 | 2.60 |
| EB Conversion, % | | 21.75 | 22.44 | 24.60 | 26.19 | 24.87 | 26.66 |
| Xylene Loss/EB Conversion, % | | 14.16 | 13.55 | 13.00 | 10.11 | 9.62 | 9.75 |
| PX Approach to Equilibrium, % | | 99.51 | 99.75 | 100.00 | 100.50 | 101.40 | 101.57 |

*Zinc content is based on bound catalyst.

These results show that isomerization carried out using the zeolite catalyst with added zinc component results in low xylene loss while maintaining high ethylbenzene conversion.

FIG. 2 graphically presents results such as are shown in Table 2.

Further test runs were made using ZSM-5 zeolite with added zinc after the catalyst had been stored for a period of time and the advantage of reduced xylene loss was only about one-third that originally achieved. It is not yet completely understood what problems result upon storage of the catalyst.

Runs were made using ZSM-5 with added cadmium, added magnesium or added barium in the low pressure, no hydrogen addition isomerization reaction. Using magnesium as an added component did not appear to result in achievement of reduced xylene losses at high ethylbenzene conversion until the temperature was raised to approximately 690° F. With zinc, cadmium and barium, the advantage of reduced xylene loss was noted at start-of-run temperatures of approximately 640° F., 640° F. and 655° F., respectively.

Unlike the catalyst containing zinc, the cadmium/ZSM-5 catalyst gave similar improved results (reduced xylene losses), both as a freshly prepared catalyst and after storage.

FIG. 3 graphically shows results for isomerization with bound ZSM-5 catalyst and bound ZSM-5 impregnated with various metals.

TABLE 4

| Xylene Loss/Ethylbenzene Conversion | |
|---|---|
| | Percent |
| Cd, Zn | 9.5 |
| Fe | 10.0 |
| Ba | 10.2 |
| Sn, Cs | 10.5 |
| La | 11.6 |
| Cu, Ni | 11.7 |
| K | 12.1 |
| Th | 14.0 |
| ZSM-5 | 13.2 |

Table 4 shows the results of xylene isomerization experiments run with various catalysts which had difference metals impregnated into the respective catalysts.

The isomerization reaction conditions included an ethylbenzene conversion of about 25 percent, a WHSV of 5.0, pressure of 25 psig, and with the data tabulated being gathered after 60 hours of onstream time for the respective catalysts. The temperature ranged between 620° F. and 670° F. and was that required with the various catalysts to achieve 25% ethylbenzene conversion.

The catalysts were prepared using the procedure in Example 5. The amount of impregnated metal was adjusted to be between 0.007 and 0.008 gm-mole per 100 gms. of the ZSM-5. This is also equivalent (in gm-mole) to about 0.5 wt. % zinc based on ZSM-5.

The results shown in Table 4 illustrate that La, Cu, Ni, K and Th did not give markedly improved xylene loss, whereas Sn, Cs, Ba, Fe, Cd and Zn did. Ba, Fe, Cd and Zn were found to be especially beneficial at the 0.007 to 0.008 gm-mole level in reducing xylene loss. Cd and Zn were found to be the most beneficial in reducing xylene loss.

TABLE 5

| Impregnated Metal Concentration in ZSM-5, Expressed as Zinc wt. % | Impregnated Metal | Catalyst Activity, Expressed as Start-of-Run Temperature, °F. |
|---|---|---|
| 0 | none | 600 |
| .25 | Cd | 630 |
| .50 | Cd | 640 |
| 1.0 | Cd | 665 |
| 4.3 | Mg | 690 |
| 0.5 | Zn | 640 |
| 0.5 | Ba | 655 |
| 0.5 | Fe | 640 |
| 0.5 | Sn | 605 |
| 0.5 | Cs | 640 |
| 0.5 | La | 610 |
| 0.5 | Cu | 620 |
| 0.5 | Ni | 615 |
| 0.5 | K | 627 |
| 0.5 | Th | 622 |

Table 5 shows the results of xylene isomerization experiments run with catalysts having varying amounts of impregnated metals.

The isomerization reaction conditions included an ethylbenzene conversion of about 25 percent, a WHSV of 5.0, and pressure of 25 psig.

The catalysts were prepared using the procedure described in Example 5. The amount of impregnated metal is based on weight percent ZSM-5. The impregnated metal is expressed as zinc weight percent by taking into consideration the atomic weight of the impregnated metal so that the gm-moles of the impregnated metal are the same as would be the gm-moles of zinc at the indicated weight percent.

The results shown in Table 5 for the Cd impregnated catalyst illustrate that raising the weight percent metals in the catalyst causes the activity of the catalyst to be reduced. Thus, to achieve a given level of conversion the start-of-run temperature is higher at higher levels of impregnated metals. For Mg impregnated catalyst the start-of-run temperature at 4.3 weight percent zinc equivalent was 690° F. This is an unacceptably high temperature. Run life with the catalyst is too short if the starting temperature is as high as 690° F.

For catalysts with various other impregnated metals at the 0.5 weight percent level the start-of-run temperature is also shown in Table 5. Many of these metals resulted in attractive start-of-run temperature, but are not within the scope of the present invention because the xylene loss was too great.

What is claimed is:

1. A process for isomerization of a non-equilibrium mixture of xylenes containing ethylbenzene which comprises:
   (a) feeding the mixture of xylenes to a xylene isomerization reaction zone;
   (b) contacting the mixture in the reaction zone with a ZSM-5 or ZSM-11 zeolite catalyst containing 0.05 to 1.5 weight percent based on zeolite of zinc, cadmium, iron, barium, tin or cesium metal, thereby isomerizing the xylenes; and
   (c) carrying out the xylene isomerization in the absence of added hydrogen, and at vapor phase reaction conditions including a temperature between 500° F. and 900° F. and a pressure between 10 and 100 psig.

2. A process in accordance with claim 1 wherein the catalyst comprises ZSM-5 zeolite, and the metal is zinc, cadmium, iron or barium, and the temperature is between 500° F. and 800° F.

3. A process in accordance with claim 1 wherein the catalyst comprises ZSM-5 zeolite and an alumina binder.

4. A process in accordance with claim 2 wherein the amount of zinc, cadmium, iron or barium is between 0.1 and 1.0 weight percent based on the zeolite.

5. A process in accordance with claim 2 wherein the xylene isomerization is carried out at a pressure between 10 and 100 psig.

6. A process in accordance with claim 2 wherein the mixture of xylenes is fed at a weight hourly space velocity in the range of 1 to 10.

7. A process in accordance with claim 5 wherein the catalyst contains between 0.1 and 1.0 weight percent of zinc or cadmium based on the zeolite.

8. A process in accordance with claim 5 wherein the catalyst consists essentially of cadmium, ZSM-5 and an alumina binder.

9. A process in accordance with claim 2 wherein the mixture of xylenes comprises metaxylene and orthoxylene and the xylenes are isomerized to paraxylene.

* * * * *